United States Patent [19]

Ballew

[11] Patent Number: 4,913,139

[45] Date of Patent: Apr. 3, 1990

[54] METHOD OF TRANSLARYNGEAL RETROGRADE TRACHEAL INTUBATION

[76] Inventor: Donald H. Ballew, 402 S. 12th Ave., Yakima, Wash. 98902

[21] Appl. No.: 308,850

[22] Filed: Feb. 9, 1989

[51] Int. Cl.$^4$ ............................................. A61M 15/00
[52] U.S. Cl. .............................. 128/200.11; 128/207.14
[58] Field of Search ...................... 604/53; 128/200.26, 128/200.11, 207.14, 207.15

[56] References Cited

U.S. PATENT DOCUMENTS

| | | | |
|---|---|---|---|
| 4,231,365 | 11/1980 | Scarberry | 128/207.15 |
| 4,244,363 | 1/1981 | Anderson | 128/200.26 |
| 4,278,081 | 7/1981 | Jones | 128/207.15 |
| 4,431,005 | 2/1984 | McCormick | 128/207.14 |
| 4,637,388 | 1/1987 | Melendy | 128/207.15 |
| 4,655,214 | 4/1987 | Linder | 128/207.18 |
| 4,672,960 | 6/1987 | Frankel | 128/207.14 |

OTHER PUBLICATIONS

Anesthesiology Review, Mar. 1983.
"Solving a Difficult Intubation," Anesthesiology, vol. 64, No. 4, Apr. 1986, pp. 537–538.
"Translaryngeal Guided Intubation Using a Sheath Stylet," Anesthesiology, vol. 65, No. 5, Nov. 1985, p. 567.
"Retrograde Intubation of the Trachea," Ann. Emerg. Med., Jun. 1987; 16:680–682.
"Endotracheal Intubation using Translaryngeal Guided Intubation vs. Percutaneous Retrograde Guidewire Insertion," Critical Care Medicine, Feb. 1987, vol. 15, No. 2, p. 183.

Primary Examiner—Jerome L. Kruter
Attorney, Agent, or Firm—Patrick M. Dwyer

[57] ABSTRACT

A method of translaryngial retrograde tracheal intubation is disclosed which employs a guide wire 30 having flexible configurations on both ends. A superior end 34 having a magnet 33 therein for cooperation with a magnetic retrievel device is also disclosed. A balloon introducer 10 is disclosed for insertion into a standard endotracheal tube 20 such that after threading the superior end 34 of the orally retrieved guide wire through the tip of the introducer and out the distal end of the endotracheal tube, the endotracheal tube and introducer may be threaded through the oral pharynx 60, through the glottic opening 66, and the vocal chords 67 with minimal trauma to surrounding tissue. A method is disclosed wherein the interior end 32 of the guide wire is not retained at the insertion site, but is instead advanced inferiorally entirely into the trachea for anchoring in the tracheal tree, followed by guided insertion of an endotracheal tube 20 with a cooperating introducer 10 to minimize wandering of the tube upon the guide wire.

5 Claims, 4 Drawing Sheets

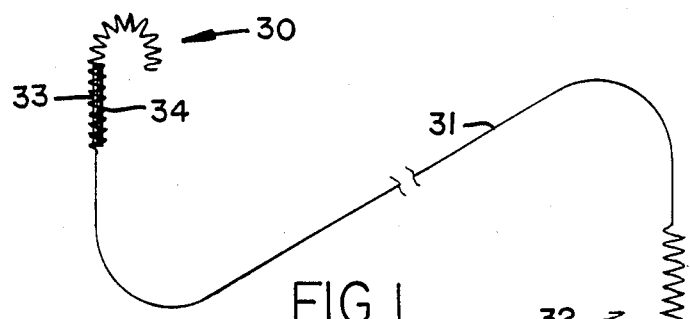
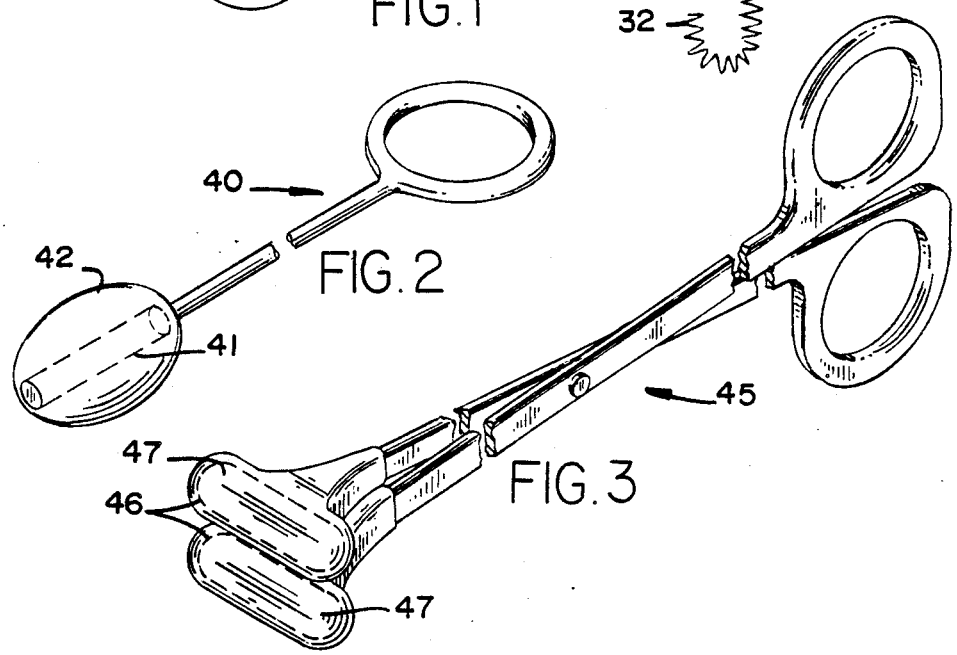
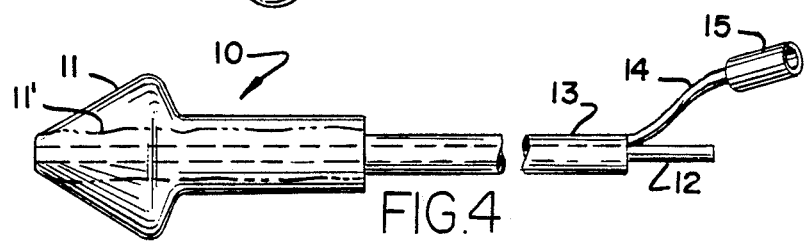
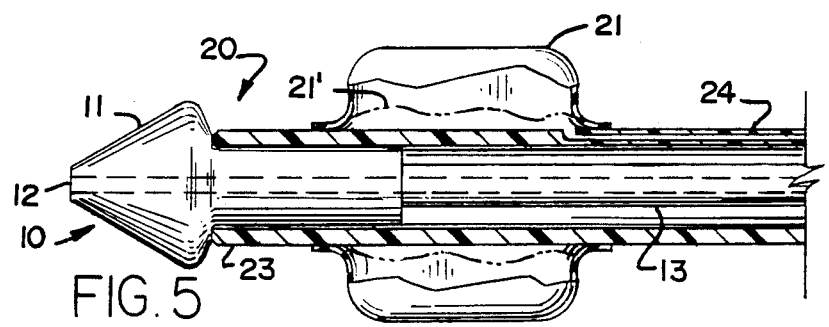

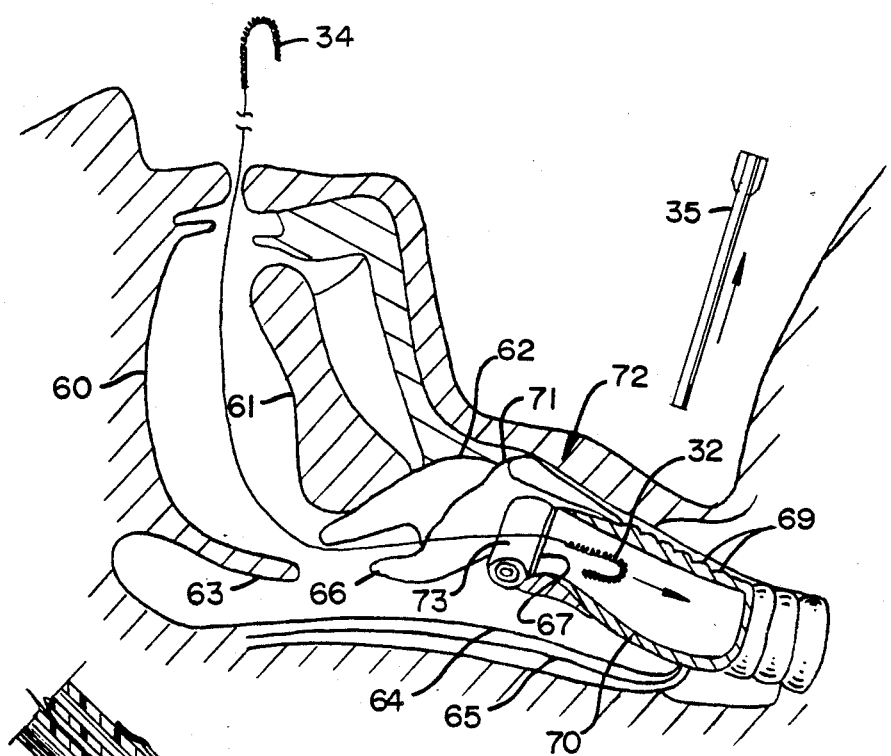
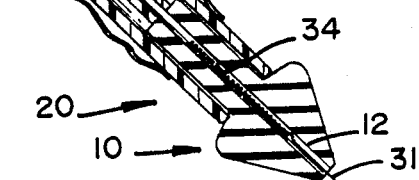
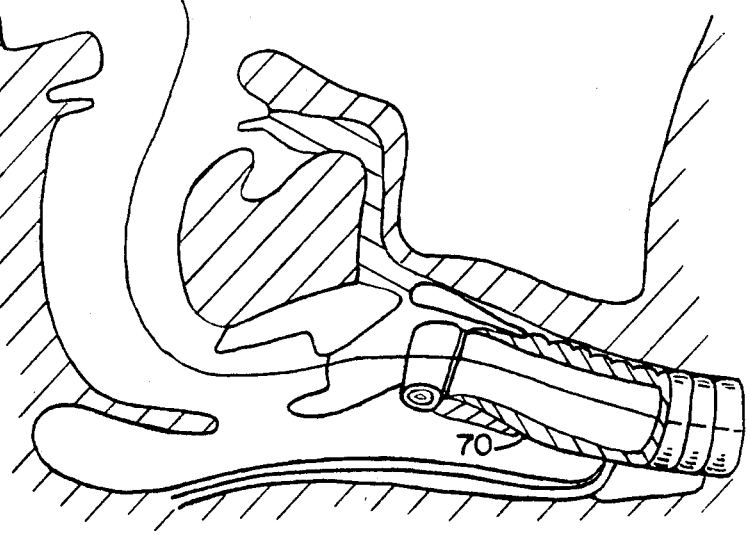
FIG.6c
FIG.6d

METHOD OF TRANSLARYNGEAL RETROGRADE TRACHEAL INTUBATION

TECHNICAL FIELD

This invention relates to the field of medical and surgical practices and more particularly to the subfield of airway management by endotracheal intubation. The invention consists of method and apparatus for a system of retrograde endotracheal intubation by employing a percutaneous guide wire insertion via hollow needle through the trachea.

BACKGROUND OF THE INVENTION

The establishment of an adequate airway is the first critical step in the resuscitation of a seriously ill or injured patient. Tracheal intubation is the preferred method for establishing an adequate airway in these circumstances. There are both a standard method of endotracheal intubation and several experimental systems. Conventional endotracheal intubation consists of the passage of a tube into the trachea. This conventional tube is open at both ends and contains a standard 15 mm adapter for attachment of a conventional bag valve or other conventional resuscitation device. When an inflatable membrane or cuff located near the end of the endotracheal tube is inflated, the airway is sealed. This allows intermittent positive pressure ventilation to be carried out and protects the airway from aspiration of foreign material. The current standard method involves the use of a malleable stylet which is inserted into the endotracheal tube so that the tube will conform to the desired configuration. The end of the stylet must always be recessed at least 1½ inches from the tube opening to prevent trauma during intubation. A laryngoscope is then employed to achieve visualization of the glottis and vocal chords, followed by insertion of the endotracheal tube with stylet through the vocal chords and into the trachea.

The laryngoscope is a device used for exposure of the glottis. It consists of a blade and handle. The handles are interchangeable, and the blade may be curved or straight. The head is then positioned to obtain the proper orientation with respect to the neck. Three axes, those of the mouth, the pharynx, and the trachea, must be aligned with respect to each other to achieve direct visualization of the trachea. In order to accomplish this objective, the neck must be flexed forward and the head must be extended backward. This puts the head into a "sniffing" position. The head must not be allowed to hang over the end of a bed or table. At the very least the occiput of the head should be on the same horizontal plane as the back of the shoulders, with the neck somewhat elevated. In most cases, it is helpful to place a few layers of toweling under the occiput to elevate it a few inches above the level of the bed. The blade of the laryngoscope is then inserted into the mouth following the natural contour of the pharynx. Once visualization of the glottic opening has been achieved with the laryngoscope the endotracheal tube is directly inserted into the larynx and trachea. In order to accomplish this maneuver, it is necessary to place the laryngoscope blade either under the epiglottis or into the space between it and the base of the tongue. A laryngoscope is employed by exerting traction upward on its handle, displacing the base of the tongue and the epiglottis anterially and exposing the glottic opening. In the process of this exposure the entire laryngoscope is pulled in a perpendicular direction directly away from the patient's head, with considerable attendant stress to the surrounding tissue in the head and the spine of the patient. Upon visualization of the epiglottis the endotracheal tube is passed between the vocal chords anterior to the arytenoid cartilages.

In emergency endotracheal intubation, with its attendant risk of regurgitation and aspiration of gastric contents, the Sellick Manoeuver is employed to apply firm pressure over the cricoid cartilage in order to occlude the upper end of the esophagus. An assistant applies firm backward pressure to the cricoid until intubation has been completed and the endotracheal tube cuff inflated.

Tracheal intubation achieves total control over the airway. This protects the airway from aspiration of foreign material and allows for intermittent and positive pressure ventilation with 100% oxygen. It makes the trachea and the respiratory tract available for suctioning. It further eliminates the problems of gastric distention associated with mouth-to-mouth or bag-valve mask ventilation. The disadvantages of this standard method are several. It requires a physician skilled in endotracheal intubation in a situation where one is not always available, or where she may be otherwise occupied with other life saving procedures on the patient. Also the present method takes several minutes, even in the hands of a skilled physician, and too often results in trauma to the tracheal and pharyngeal tissues as well as sometime intubation of the esophagus and stomach resulting in dangerous vomiting. In the standard method it is necessary to auscult the chest as soon as possible after intubation to make certain that the lungs are being ventilated. The epigastric area may be auscultated after a tracheal intubation and after chest auscultation to confirm that the tube is in the trachea and not in the esophagus, which would require reintubation. In addition there is risk of injury to the spine, particularly where there are already attendant spinal injuries. Finally anatomic distortions, either congenital or caused by the injuries, may further hamper or completely frustrate the use of the standard method.

The experimental systems all require retrograde nasal or oral insertion of an endotracheal tube along a guide wire. The experimental systems all require insertion of a hollow core needle percutaneously into the intracrycoid space of the trachea. A guide wire is then inserted translaryngially through the hollow needle in the intercrycoid space through the trachea, superiorly up through the pharynx and out of the mouth or nose. There follows then a guided insertion of a standard endotracheal down the guide wire into the trachea. The guide wires employed in current experimental methodology all employ some kind of flexible configuration at the inserted end of the guide wire, while the retained end of the guide wire at the intercrycoid insertion site remains stiff and unused. In known experimental methods, once the guide wire is advanced into the oral pharynx it is either allowed to pass fortuitously out of the mouth or nose or else it is retrieved with forceps. The guide wire is then pulled out through the mouth or nose to a length which is greater than the length of the endotracheal tube to be used. Typically, the hollow needle is removed after the guide wire with its flexible superior tip has been inserted into the trachea. One experimental method calls for the insertion of the guide wire into the lumen, or side hole, of the standard endotracheal tube in order to minimize "wandering" of the tube as it progresses inferiorally through the pharyngeal cavity and down towards the glottic opening into the trachea to the point of the needle's insertion. This positioning of the guide wire in the lumen also allows the insertion of the endotracheal tube an extra centimeter or so beyond the point of the guide wire's intercrycoid insertion. At this point in all of the experimental methods, the guide wire is then removed. In some methods the endotracheal tube is then further advanced into the trachea. Once at an appropriate position the circumferential balloon or inflatable cuff of the endotracheal tube is inflated and the patient is intubated.

These known experimental methodologies call for a large diameter, relatively inflexible, endotracheal tube to be advanced over a small diameter, relatively flexible, guide wire down into the trachea. The guide wire remains inserted in the intracrycoid transit site, and is even used as leverage point to assist in the advancement of the endotracheal tube. There are several disadvantages of these current experimental intubation systems.

First, it is difficult to locate and retrieve the end of the currently employed guide wires in the oral pharynx because of the size of the guide wire and the lack of direct visualization. These problems may be exacerbated in emergency situations.

Second, the advancement of the endotracheal tube over the guide wire and stiff nature of the retained end of the guide wire at the tracheal insertion point of the wire create significant leverage pressure upon the tissue at the guide wire's intracrycoid insertion point because the point acts as a fulcrum during the advancement procedure. This can cause significant trauma to the tissue surrounding the insertion point, such as tearing or hemorrhaging, trauma which can be especially severe as a result of excessive advancement of the endotracheal tube beyond the point of insertion during rapid emergency procedures because the guide wire is then forcibly thrust downwardly against delicate tissue. This excessive advancement can and does easily occur in these emergency situations.

Third, even with a lumen or side hole insertion of the guide wire into the endotracheal tube, and especially without such insertion, the relatively large diameter endotracheal tube is allowed to float significantly from the guide wire's path during intubation, and this "wandering" can cause significant trauma to various tissues in the pharyngeal and laryngeal paths, particularly to the vocal chords. Occasionally the trauma can be so severe as to result in obstruction of the endotracheal tube's passage into the trachea.

Fourth, the conventional endotracheal tube is both blunt and stiff on its advancing inferior end and that bluntness and stiffness can also result in significant trauma to surrounding tissues and structures, primarily to the vocal chords, as the endotracheal tube is advanced.

DISCLOSURE OF INVENTION

Accordingly it is an object of the invention to provide method and apparatus for establishing an emergency airway which does not require a physician skilled in endotracheal intubation.

It is a further object of the invention to provide a method for establishing endotracheal intubation which minimizes trauma to surrounding tissue and which can be accomplished in substantially less time than current methods, and which is more certain to avoid unintentional intubation of the esophagus.

It is another object of the invention to provide a method and apparatus of easily locating and retrieving in the oral pharynx the end of a translaryngially inserted guide wire.

It is a still further object of the invention to provide a method whereby a guide wire having flexible configurations on both ends of the wire is fully drawn through the insertion needle and into the trachea so as to avoid creating leverage pressure on tissue at the insertion site.

It is another object of the invention to provide method and apparatus of cushioning the inserted end of the standard endotracheal tube with an inflatable introducer having a narrow internal diameter so as to both cushion the inserted passage of the endotracheal tube toward the glottic opening of the trachea and to minimize "wandering".

These and other objects of the invention are accomplished by the method and with the apparati more particularly disclosed herein. The invention comprises both method and several apparati directed to achieving the above objects.

The method of the invention comprises the steps of (1) percutaneous insertion of a guide wire having two flexible ends via a hollow needle through the intracrycoid space in the trachea; (2) superior advancement of the inserted end of the guide wire up into the oral pharynx; (3) retrieving the inserted, superior end of the guide wire in the oral pharynx by insertion of a magnetized wand or magnetized forceps into the mouth to retrieve the inserted end of the guide wire which also contains therein a magnet; (4) withdrawal of the superior end of the guide wire out of the mouth such that the withdrawal of this superior end pulls through the hollow needle at the insertion site the inferior flexible end of the guide wire; (5) removal of the hollow needle from the insertion site; (6) threading the guide wire inferiorally down into the trachea until the inferior flexible tip is anchored in the tracheal tree, such that the length of guide wire protruding from the mouth which remains is long enough to pass all the way through the appropriate endotracheal tube with its inflated introducer tip installed; (7) insertion of the retrieved end of the guide wire into an introducer, which has been previously installed into a standard endotracheal tube and inflated, and advancing the superior end of the guide wire through the length of the introducer and tracheal tube; (8) guided insertion of the endotracheal tube and introducer along the guide wire through the glottic opening and the vocal chords into the trachea; (9) inflation of the endotracheal tube's cuff to seal the airway; and (10) deflation and withdrawal of the introducer and guide wire from the endotracheal tube. The inferior placement of the guide wire will also prevent its displacement outside of the glottal mechanism.

The apparatus of the invention comprises a flexible guide wire which has flexible configurations on both the inserted superior end and on the inferior end, the superior flexible end having a magnet incorporated therein for cooperating with apparatus in the form of a magnetic wand or forceps inserted into the pharyngeal cavity orally to magnetically retrieve the superior end.

The apparatus of the invention also comprises an inflatable introducer. The introducer provides a tapered semi-soft advancing surface for the endotracheal tube while a small diameter hollow channel located therein is threaded over the guide wire so that the whole assembly of introducer and endotracheal tube more exactly follows the guide wire path to substantially eliminate the wandering associated with known experimental methods of intubation over a guide wire. The introducer is deflatable and removable after the endotracheal tube is in position.

BRIEF DESCRIPTION OF THE DRAWINGS

FIG. 1 is a plan view of an embodiment of the guide wire apparatus of the invention.

FIG. 2 is an isometric view of an embodiment of the magnetic wand apparatus of the invention.

FIG. 3 is an isometric view of an alternate embodiment of the magnetic retrieving apparatus of the invention.

FIG. 4 is side elevation of an embodiment of the introducer apparatus of the invention.

FIG. 5 is a partial side elevation of the tube assembly with the endotracheal tube shown in partial section.

FIG. 6 comprising FIGS. 6A-6F are sectional views of a human head and neck illustrating the method of the invention.

BEST MODE OF ACCOMPLISHING THE INVENTION

Figure 6A:
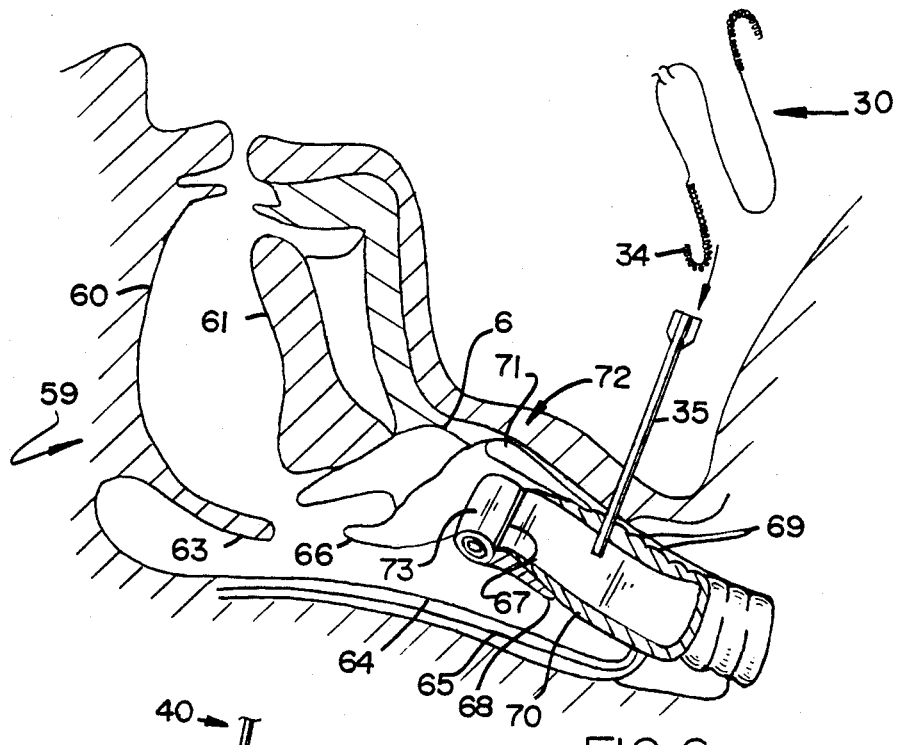

Referring now to the drawings wherein like numbers indicate like parts, an embodiment of a guide wire 30 is shown in FIG. 1 having conventional wire 31 and conventional flexible configuration superior tip 34, shown in the form of a conventional "J", further having within the coil of tip 34 a magnet 33. Guide wire 30 has an inferior flexible tip 32, shown also in the "J" configuration. Other flexible configurations for both tips 34 and may be employed without departing from the scope of the invention. The flexible tip configurations 32 and 34 and the wire 31 are made of materials and by methods well known in the art. Optionally magnet 33 may be eliminated for use of guide wire 30 in circumstances where retrieval of superior end 34 in the oral pharynx will not be a problem, such as when for one reason or another direct visualization of flexible tip 34 will be possible. Magnet 33 is preferably a powerful thin cylinder magnet with the tip configuration of tip 34 wound around it and enclosing it therein.

FIG. 2 shows a retrieval wand 40 having a relatively soft bulbous tip 42 within which is enclosed a magnet 41. Wand 40 is preferably made of some flexible and inexpensive plastic material, but any material may be employed in any shape or configuration without departing from the scope of the invention. A soft bulbous tip is only preferred to reduce the possibility of injury to adjacent tissue. Magnet 41 is preferably a compact extremely powerful magnet which may be inserted into tip 42 and retained therein by any of several conventional methods, such as casting the plastic material of the tip around the magnet, or drilling the tip for insertion of appropriately sized magnet, followed by interference retention or gluing of magnet 41 within tip 42.

As an alternative to wand 40 an otherwise conventional forceps 45 shown in FIG. 3 may be employed which has spatulate tips 46 each of which contain a magnet 47. Forceps 45 may be composed of some relatively rigid plastic material or other conventional forceps material. Magnets 47 are embedded in tips 46 in a manner similar to those disclosed for wand 40. Alternatively, the forceps 45 may be made of a ferrous substance and the entire forceps magnetized.

In FIG. 4 is shown a balloon introducer 10 which is comprised of a hollow guide tube sheath 13 enclosing guide tube 12 which runs substantially along the longitudinal axis of sheath 13. Guide tube sheath 13 runs substantially the length of guide tube 12 and communicates through air tube 14 with conventional syringe adapter 15. This rearward portion of introducer 10 is substantially identical to the arrangement found in the corresponding rearward portion of a conventional balloon angiocatheter, except that there need be no syringe adapter attached to the end of guide tube 12. The forward portion of introducer 10 is comprised of a continuation of guide tube sheath enclosing guide tube 12 out to the very forward tip of introducer 10 and balloon sheath 11 which has a forward most portion which is conically shaped and a more rearward portion which is cylindrically shaped, both to function as is more particularly described below.

Balloon sheath 11 communicates with hollow guide tube sheath so that air injected via a syringe at syringe adapter 15 through air tube 14 serves to inflate balloon sheath 11 in a well known manner. Balloon sheath 11 is shown in its deflated position at 11'. In a preferred embodiment balloon sheath 11 is made of the same material as the balloon portion of a conventional balloon angiocatheter and has a conical forward portion which, when inflated, widens to a maximum diameter and then tapers gradually back to a more rearward cylindrically shaped portion. However other forward shapes of inflated balloon sheath 11 such as hemispherical will serve as well. The conical shape of inflated sheath 11 serves to guide the introducer and its associated endotracheal tube gently and surely through the tracheal and pharyngial passages with minimal trauma to tissue. The gradual tapering of the inflated rearward portion of the conically shaped portion of introducer sheath 11 to the more cylindrical portion, and the cylindrical portion itself serve to hold introducer 10 within an endotracheal tube so that their respective axes are substantially aligned.

In FIG. 5 is shown an endotracheal tube 23 which varies from the structure of a conventional endotracheal tube in that the tip of tube 23 terminates in a substantially blunt configuration adapted to cooperate with the rearward tapering portion of the conically shaped front end of introducer sheath 11 instead of having the tip of the endotracheal tube slant pointed like the tip of a hollow syringe needle. Tube 23 includes conventional inflation cuff 21 (shown deflated at 21') which communicates rearwardly through integral inflation tube 24 to a source of pressurized air in a conventional manner. Since the rearward portion of endotracheal tube assembly 20 consists only of conventional structures, it has not been illustrated. Once deflated introducer 10 has been inserted into endotracheal tube 23 so that the conical tip of introducer sheath 11 protrudes from tube 23, balloon sheath 11 is then inflated to provide a semi-soft advancing tip for the endotracheal tube assembly 20 and to hold introducer 10 firmly within tube 23 in such a way that guide tube 12 can receive a superior end of guide wire 30 and then be advanced down wire 31 without "wandering."

Figure 6B:
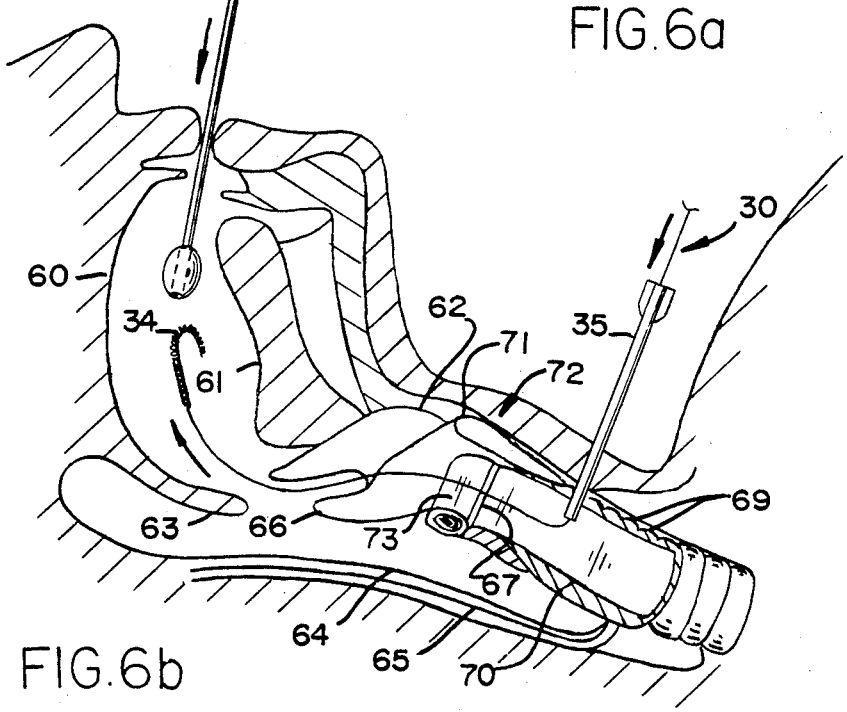
Figure 6E:
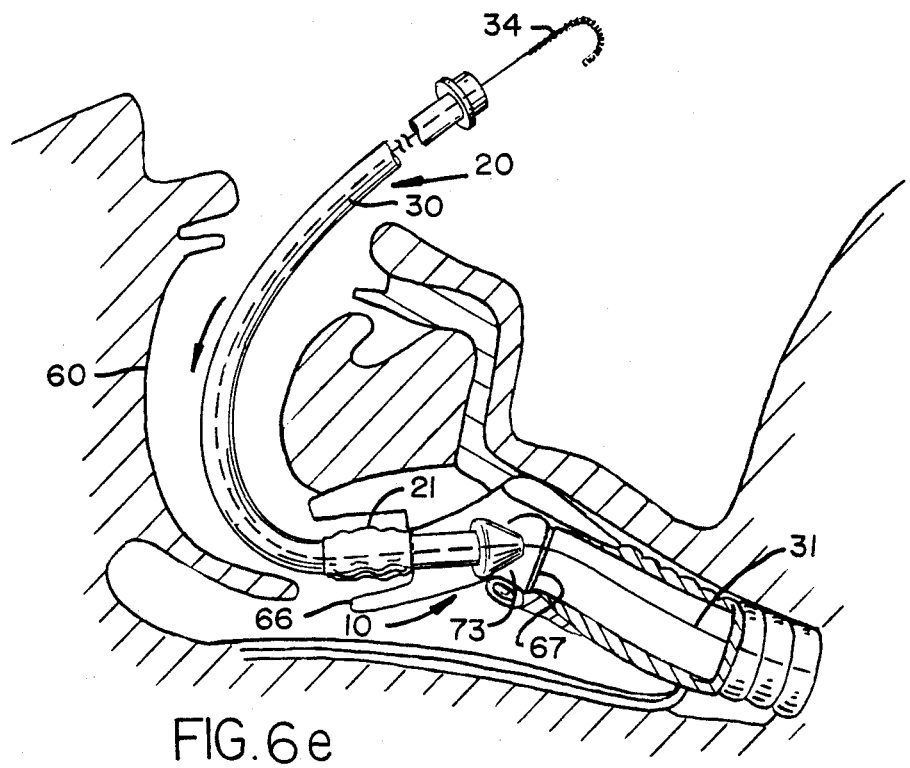
Figure 6F:
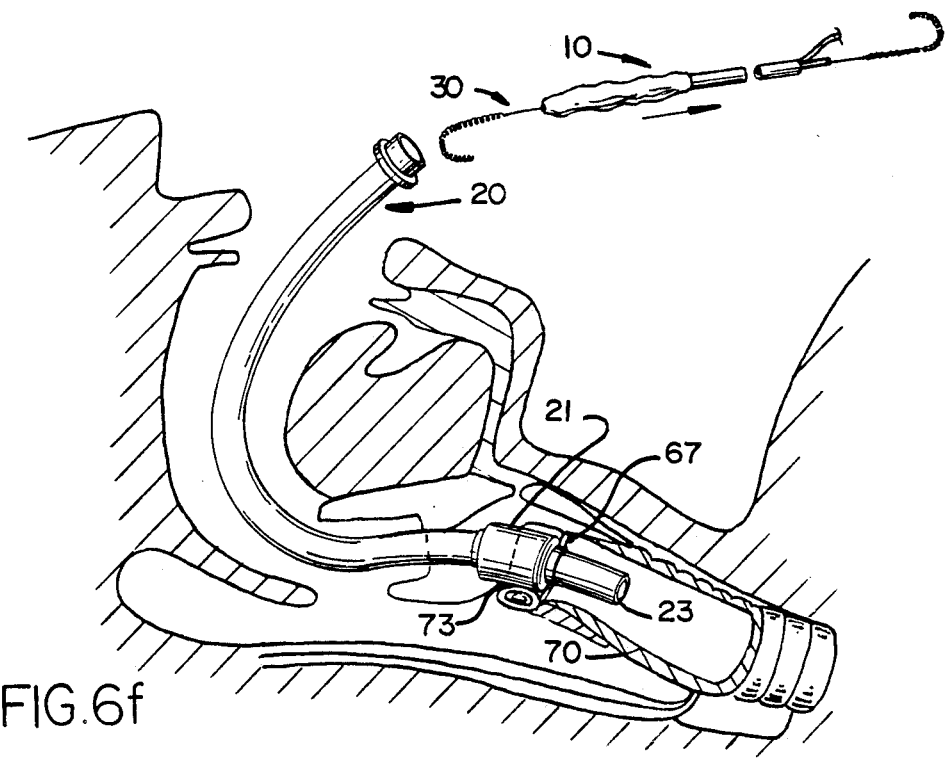

FIGS. 6A-6F illustrate an embodiment of the method of the invention. Patient 59 is positioned supine and hollow needle 35 is inserted percutaneously, as per standard medical practice, in the inferior portion of the crycoid cartilage 68 just below larynx 72 and thyroid cartilage 71. Needle 35 is tilted caudad (not shown) and flexible superior tip 34 of guide wire 30 is inserted therethrough in a conventional manner and into trachea 70. Typically, needle 35 is inserted between a pair of tracheal rings 69 (so called intracrycoid space). Guide wire 30 is then advanced superiorally through needle 35, up trachea 70 between vocal chords 67, past epiglottis 66 and hyoid bone 62, past uvula 63 and into oral pharynx 60, where magnet enclosing flexible tip 34 is retrieved by wand 40 as more particularly described above.

Once flexible tip 34 has been drawn out of the mouth of patient 59 the rest of guide wire 30 is then pulled through needle 35 until inferior flexible tip 32 just passes into trachea 70. Needle 35 is then withdrawn, and guide wire 30 is then advanced inferiorly down into trachea 70 in the direction of the arrow illustrated in trachea 70 (FIG. 6C) until inferior tip 32 can be lodged somewhere in the tracheal tree (not shown). Guide wire 30 is sized so that when flexible tip 32 is lodged in the tracheal tree, sufficient length of wire 31 protrudes from the mouth to exceed the length of the full endotracheal tube assembly 20.

With the lower tip of the inferior tip 32 of guide wire anchored in the tracheal tree, flexible tip 34 is then straightened and inserted into guide tube 12 of endotracheal tube assembly 20. Alternatively tip 34 may be cut from wire 31, and the cut end of the wire inserted into tube 12. Conventional J-point wires come equipped with a plastic straightening sheath which is slid backwardly as the wire is advanced thru the insertion needle. Preferably, the apparatus of the invention employs such a sheath (not shown) which is split longitudinally so that it may be removed after the straightened J-point tip 34 is inserted into needle 35. Thereafter, the split sheath, or a spare like it, is retained and is slid over wire 31 and up onto and around tip 34 after it is retrieved from the mouth. Thus tip 34 is once again straightened for insertion into guide tube 12. After insertion, the split sheath is slid backwardly and then removed More wire 31 is then fed into guide tube 12 until flexible tip 34 emerges from the opposite end of tube assembly 20 (not shown). At this point tube assembly 20 is in the position shown in FIG. 6D just about to enter the mouth of the patient.

Endotracheal tube assembly 20 is then passed along guide wire 30 with introducer 10 leading the way past soft tissue, past epiglottis 66, and into the laryngeal pharynx 73. The flexible superior tip 34 of guide wire 30 is retained in one hand of the person administering the intubation while the other hand advances endotracheal tube assembly 20 along guide wire 30 in a well known manner. The direction of advance is the direction shown by the arrow in FIG. 6E. During this portion of the intubation procedure inflation cuff 21 is not inflated. The tip of introducer 10 then passes (not shown) through vocal chords 67, continuing to be guided by guide wire 30 until endotracheal tube assembly 20 is in the position shown in FIG. 6F. Inflation cuff 21 is then inflated in the laryngeal pharynx 73 to seal the tracheal airway, the forward portion of tube 23 having progressed retrograde to a position inferior of the vocal chords 67. When endotracheal tube assembly 20 is in this position and inflation cuff 21 is inflated to seal the airway, introducer 10 is deflated and withdrawn together with guide wire 30 from tube assembly 20 and the patient is intubated. In compliance with the statute, the invention has been described in language more or less specific as to structural features. It is to be understood, however, that the invention is not limited to the specific features shown, since the means and construction shown, comprise preferred forms of putting the invention into effect. The invention is, therefore, claimed in any of its forms or modifications within the legitimate and valid scope of the appended claims, appropriately interpreted in accordance with the doctrine of equivalents.

INDUSTRIAL APPLICABILITY

The method and apparatus of the invention will find use in hospitals and emergency rooms wherever an emergency airway must be established in a human patient. The invention is an improvement over all existing systems of emergency airway management in that a skilled physician is not required to establish the airway using the method and apparatus of the invention; the method and apparatus allow quick and sure establishment of an airway directly to the trachea; the parts of the apparatus will either be standard disposable equipment or specially manufactured equipment which will be relatively inexpensive and also disposable. The method and apparatus of the invention will be of material assistance in emergency and lifesaving procedures.

I claim:

1. A method of guided retrograde endotracheal intubation comprising the steps of:
   (a) percutaneous translaryngeal insertion of a guide wire into a trachea, said guide wire having a superior, flexible configured tip;
   (b) superior advancement of said guide wire and retrieval of said superior flexible tip in an oral pharynx;
   (c) threading said superior flexible tip into and through an endotracheal tube assembly, said tube assembly having therein and inflated introducer so arranged and structured that a flexible tip of said introducer protrudes at the forward end of said tube assembly, said introducer having disposed longitudinally within it a guide tube for receiving said superior flexible tip and said guide wire;
   (d) guiding said tube assembly inferiorly along said guide wire so that said tip of said introducer passes inferiorly through the oral pharynx, through a glottal opening and between the vocal chords; and
   (e) inflating a cuff on said tube assembly to seal the airway of said trachea, deflating said introducer, and withdrawing said introducer and said guide wire superiorally from said tube assembly.

2. The method of claim 1 wherein said guide tube has a diameter just large enough to allow free passage therethrough of said superior flexible tip.

3. The method of claim 1 wherein said superior flexible tip is further comprised of a small powerful magnet, and said step of retrieving said superior flexible tip is achieved by inserting a magnetic wand into said oral pharynx to attract and catch said superior flexible tip with said magnet.

4. The method of claim 1 wherein the inferior end of said guide wire terminates in a flexible configured tip, said method further comprising a step immediately after retrieval of said superior flexible tip in the oral pharynx of withdrawing said guide wire assembly superiorally from said oral pharynx in order to pull said inferior flexible tip just into said trachea.

5. The method of claim 4 comprising the further step, after pulling said inferior flexible tip into said trachea, of advancing said inferior flexible tip inferiorly to a position in the tracheal tree where it can be anchored, and so anchoring it.

* * * * *